(12) United States Patent
Liang et al.

(10) Patent No.: US 10,444,167 B2
(45) Date of Patent: Oct. 15, 2019

(54) DETERMINING THE LEACHING PROFILE OF A CUTTER ON A DRILLING TOOL

(71) Applicant: Halliburton Energy Services, Inc., Houston, TX (US)

(72) Inventors: Qi Liang, Richmond, VA (US); Gagan Saini, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 242 days.

(21) Appl. No.: 15/521,342

(22) PCT Filed: Nov. 24, 2014

(86) PCT No.: PCT/US2014/067109
§ 371 (c)(1),
(2) Date: Apr. 24, 2017

(87) PCT Pub. No.: WO2016/085449
PCT Pub. Date: Jun. 2, 2016

(65) Prior Publication Data
US 2017/0307547 A1  Oct. 26, 2017

(51) Int. Cl.
*G01N 23/18* (2018.01)
*G01N 23/083* (2018.01)

(52) U.S. Cl.
CPC ......... *G01N 23/18* (2013.01); *G01N 23/083* (2013.01); *G01N 2223/33* (2013.01);
(Continued)

(58) Field of Classification Search
CPC .. G01N 23/18; G01N 23/083; G01N 2223/33; G01N 2223/3308; G01N 2223/61; G01N 2223/652
See application file for complete search history.

(56) References Cited

U.S. PATENT DOCUMENTS 5,603,414 A * 2/1997 Rooney ............... G01N 23/12
                                                              209/588
6,610,181 B1 8/2003 Besser et al.
(Continued)

FOREIGN PATENT DOCUMENTS

CN        101405597        4/2009
CN        103969276        8/2014
(Continued)

OTHER PUBLICATIONS

International Search Report and Written Opinion, Application No. PCT/US2014/067109; 13 pgs, dated Jul. 29, 2015.
(Continued)

*Primary Examiner* — Courtney D Thomas
(74) *Attorney, Agent, or Firm* — Baker Botts L.L.P.

(57) ABSTRACT

In accordance with some embodiments of the present disclosure, systems and methods for determining the leaching profile of a cutter on a drilling tool are disclosed. The method includes applying an X-ray impermeable layer to a surface of a leached PCD element with residual infiltrant. The method also includes moving the element through an X-ray beam. The method further includes detecting an X-ray intensity received by an X-ray detector. The method further includes generating a leaching profile of the leached PCD element based on the X-ray intensity.

20 Claims, 5 Drawing Sheets

(52) U.S. Cl.
CPC . *G01N 2223/3308* (2013.01); *G01N 2223/61* (2013.01); *G01N 2223/652* (2013.01)

(56) References Cited

U.S. PATENT DOCUMENTS

| | | | |
|---|---|---|---|
| 6,787,326 | B1 | 9/2004 | Ratcliffe et al. |
| 7,616,734 | B1 * | 11/2009 | Corbett ................ G01N 23/223 378/46 |
| 7,712,553 | B2 | 5/2010 | Shamburger et al. |
| 7,801,268 | B1 | 9/2010 | Mourik et al. |
| 7,813,470 | B2 | 10/2010 | Kuwabara |
| 8,322,217 | B2 | 12/2012 | Bellin |
| 8,461,832 | B2 | 6/2013 | Bertagnolli et al. |
| 8,567,531 | B2 | 10/2013 | Belnap et al. |
| 8,663,349 | B2 | 3/2014 | Sani et al. |
| 9,541,511 | B2 | 1/2017 | Vigliante |
| 2010/0089663 | A1 | 4/2010 | Corbett et al. |
| 2010/0126779 | A1 | 5/2010 | Corbett et al. |
| 2010/0320006 | A1 | 12/2010 | Fan et al. |
| 2011/0061944 | A1 | 3/2011 | Scott et al. |
| 2012/0261196 | A1 | 10/2012 | Yu et al. |
| 2012/0261197 | A1 | 10/2012 | Miess et al. |
| 2013/0043078 | A1 | 2/2013 | Qian et al. |
| 2013/0092451 | A1 | 4/2013 | Mukhopadhyay et al. |
| 2013/0214769 | A1 | 8/2013 | King et al. |

FOREIGN PATENT DOCUMENTS

| | | |
|---|---|---|
| WO | 2011-029773 | 3/2011 |
| WO | 2012-135497 | 10/2012 |
| WO | 2013-098216 | 7/2013 |
| WO | 2013-098217 | 7/2013 |
| WO | 2014-020021 | 2/2014 |

OTHER PUBLICATIONS

Yahiaoui, M., et al., "A study on PDC drill bits quality," Wear, Elsevier, 2013, 298-299, pp. 32-41.
Yahiaoui, M., et al., "Analytical and Experimental Study on PDC Drill Bits Quality," 3rd European Conference on Tribology, Jun. 2011, Vienne, Austria. pp. 475, 2011.
Boland, et al., "Characterization of Diamond Composites for Tooling," CSIRO Exploration and Mining and MDU Flagship, Journal of the Australian Ceramic Society, vol. 46(1), 2010, pp. 1-10.
Bellin, et al. "The current state of PDC bit technology," World Oil, Nov. 2010 issue, pp. 67-71.
Durrand, Christopher J., "Super-Hard, Thick, Shaped PDC Cutters for Hard Rock Drilling Development and Test Results," Novatek International, Thirty-fifth Workshop on Geothermal Reservoir Engineering, Stanford University, Feb. 2010, 8 pgs.
International Preliminary Report on Patentability for PCT Patent Application No. PCT/US2014/067109, dated Jun. 8, 2017; 11 pages.
Office Action for Canadian Patent Application No. 2965343, dated Feb. 16, 2018; 3 pages.
Office Action for Chinese Patent Application No. 201280074423.7, dated Apr. 24, 2018 (no English translation); 7 pages.
Office Action for Chinese Patent Application No. 201480082735.1, dated Jul. 2, 2018 (no English translation); 6 pages.

\* cited by examiner

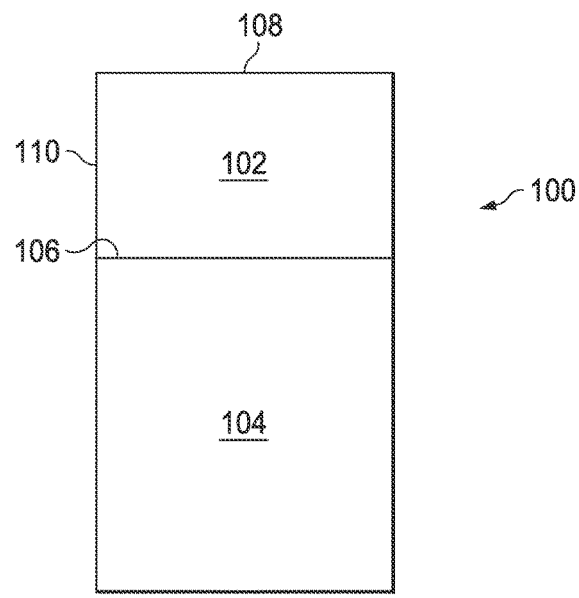
FIG. 1
FIG. 3
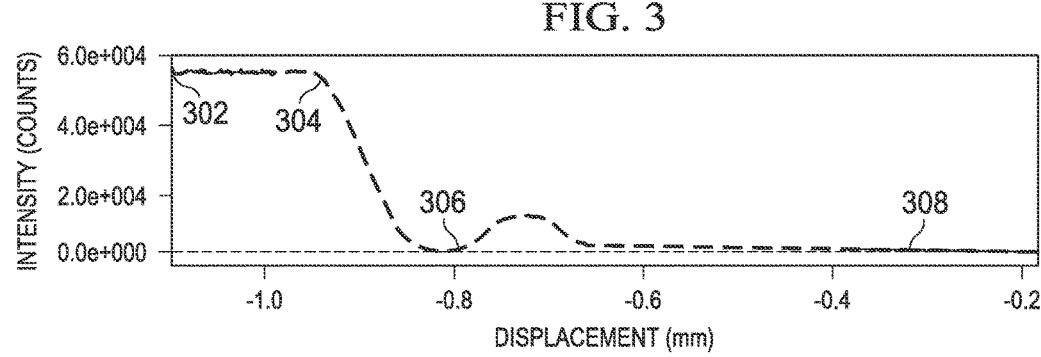

DETERMINING THE LEACHING PROFILE OF A CUTTER ON A DRILLING TOOL

RELATED APPLICATIONS

This application is a U.S. National Stage Application of International Application No. PCT/US2014/067109 filed Nov. 24, 2014, which designates the United States, and is incorporated herein by reference in its entirety.

TECHNICAL FIELD

The present disclosure relates generally to systems and methods for determining the leaching profile of a cutter.

BACKGROUND

Components of various industrial devices are often subjected to extreme conditions, such as high impact contact with abrasive surfaces. For example, such extreme conditions are commonly encountered during subterranean drilling for oil extraction or mining purposes. Diamond, with its unsurpassed wear resistance, is the most effective material for earth drilling and similar activities that subject components to extreme conditions. Diamond is exceptionally hard, conducts heat away from the point of contact with the abrasive surface, and may provide other benefits in such conditions.

Cutters and other elements for use in drilling a wellbore have a longer usable life in downhole and drilling conditions if their surface layer is made of polycrystalline diamond (PCD) or another superabrasive material, typically in the form of a polycrystalline diamond compact (PDC), or another super abrasive material compact. Cutters and other elements may contain a PCD layer bonded to a substrate. PCD may be formed at least in part from diamond powder compressed at high temperature and pressure.

The process for forming PCD often involves the use of various additives. For example, cobalt is a substance that may be added for facilitating diamond-diamond bonds in the PCD and for bonding the PCD to a substrate. Such a substance is sometimes referred to in the art of PCD manufacturing as a catalyst or catalyzing material. Substances added to diamond powder used in PCD also include binders and infiltrants. During production of the cutter or other element or before its use in a subterranean operation, the catalyst, infiltrant, or binder may be wholly or partially removed from interstices in the PCD through a removal process, such as acid leaching. PCD from which a substantial amount of catalyst, binder, or infiltrant has been removed is typically more thermally stable than corresponding PCD containing more catalyst, binder, or infiltrant and is thus often referred to as thermally stable polycrystalline diamond (TSP).

BRIEF DESCRIPTION OF THE DRAWINGS

For a more complete understanding of the present invention and its features and advantages, reference is now made to the following description, taken in conjunction with the accompanying drawings, in which:

FIG. 1 illustrates a cross-sectional side view of a thermally stable polycrystalline (TSP) diamond cutter;

FIG. 3 illustrates a graph of the X-ray intensity profile of a polycrystalline diamond (PCD) cutter leached to a depth of approximately four hundred microns, in accordance with some embodiments of the present disclosure;

DETAILED DESCRIPTION

Figure 2A:
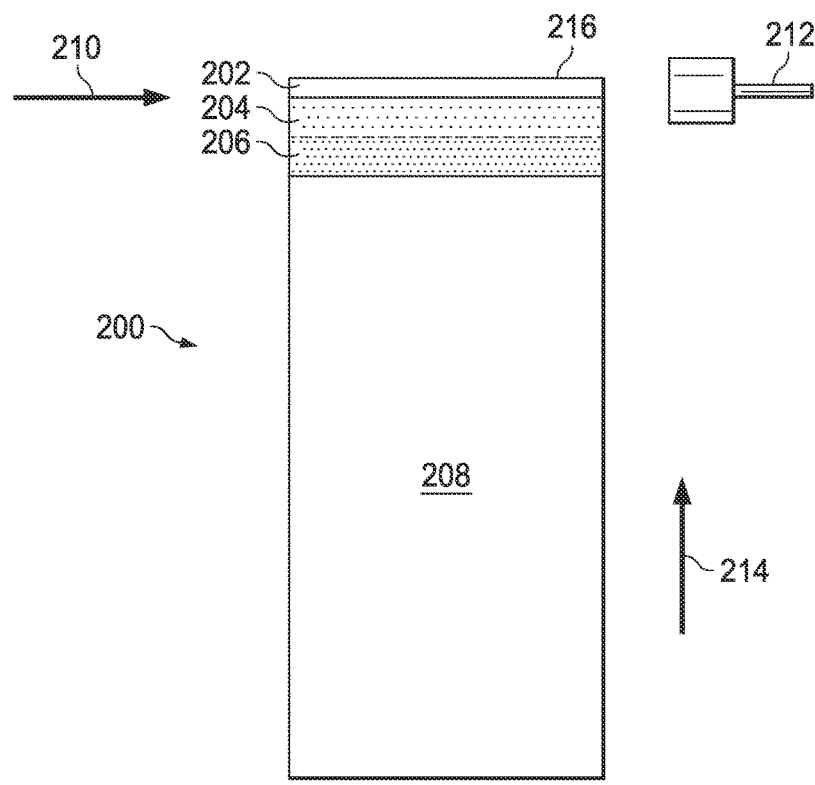
FIG. 2A illustrates a cross-sectional side view of a TSP diamond cutter including an X-ray impermeable layer, in accordance with some embodiments of the present disclosure.

The present disclosure describes a system and method for using X-rays to determine the leaching profile of a PCD cutter or other element formed from PCD. Cutters and other PCD elements used on drilling tools may include PCD bonded to a substrate. The substrate may be the drilling tool itself or a separate material, such as a metal-containing material, such as tungsten carbide. The PCD may be leached to remove substances such as catalyst, binder, and/or infiltrant materials (collectively referred to below as infiltrant(s)) from the interstices. The PCD may be leached before the PCD is bonded to the substrate, after it is bonded, or both before and after it is bonded. After any leaching process, testing may be performed on the cutter or other PCD element to determine the leaching profile of the PCD layer. The leaching profile may include the leaching depth, the amount of infiltrant remaining in the PCD layer, particularly at various locations or depths, or any other properties relating to the amount or presence of leached material. The testing may be performed by applying an X-ray impermeable layer to an outer surface of the PCD layer and measuring the intensity of X-rays as the cutter or other PCD element is passed through an X-ray beam. The X-rays are largely stopped by the X-ray impermeable layer, then pass very readily through leached diamond due to diamond's extremely high X-ray permeability. Infiltrant is less X-ray permeable than diamond, so its presence can be detected due to a decrease in X-rays passing through the PCD layer. The substrate is typically also relatively X-ray impermeable and can be detected, if present. X-ray testing is non-destructive and thus presents disclosure a more cost-effective method for determining the leaching profile of a cutter or other PCD element as compared to destructive methods, such as SEM analysis. Accordingly, the disclosure provides methods of using X-rays to determine a leaching profile of a cutter or other PCD element. The methods may have different designs, configurations, or parameters according to the particular application.

Embodiments of the present disclosure and its advantages are best understood by referring to FIGS. 1 through 8, where like numbers are used to indicate like and corresponding parts.

FIG. 1 illustrates a cross-sectional side view of a TSP diamond cutter. Diamond in its polycrystalline form has added toughness as compared to single crystal diamond due to the random distribution of the diamond crystals, which avoids the particular planes of cleavage found in single diamond crystals. Therefore, polycrystalline diamond is frequently used in many drilling applications or other extreme conditions. Cutters and other PCD elements have a longer usable life in drilling and downhole conditions if their surface layer is made of diamond, typically in the form of a PCD, such as TSP, or another super abrasive material.

Cutter 100 may contain PCD layer 102 bonded to substrate 104. The manufacturing process for cutter 100 may be very exacting and expensive. The process may be referred to as "growing" polycrystalline diamond directly onto substrate 104, which may be a carbide substrate, to form PCD layer 102. PCD layer 102 may be formed onto carbide substrate 104 by any suitable process. One example process involves placing a cemented carbide piece and diamond grains mixed with a infiltrant into a container of a press and subjecting it to a press cycle using ultrahigh pressure and temperature conditions. The ultrahigh temperature and pressure cause the small diamond grains to form into an integral PCD body. The resulting PCD layer 102 is also intimately bonded to substrate 104, resulting in cutter 100.

To create cutter 100, cobalt or other metal infiltrant systems may be used to facilitate PCD layer 102 growth. After crystalline growth is complete, the infiltrant remains within pores of PCD layer 102. Because cobalt and other metal infiltrants have a higher coefficient of thermal expansion than diamond, when PCD layer 102 is heated, e.g., during the brazing process by which substrate 104 is attached to another material, or during actual use, the metal infiltrant expands at a higher rate than the diamond. As a result, when PCD layer 102 is subjected to temperatures above a critical level, the expanding infiltrant may cause fractures in PCD layer 102. These fractures may weaken PCD layer 102 and can ultimately lead to damage or failure.

As a result of these or other effects, it common to remove the infiltrant from at least a portion of PCD layer 102, particularly portions near the working surface (e.g., top 108 or side 110). The most common process for infiltrant removal uses a strong acid bath, although other processes that employ alternative acids or electrolytic and liquid metal techniques also exist. In general, removal of the infiltrant from PCD layer 102 using an acid-based method is referred to as leaching. Acid-based leaching typically occurs first at the outer surface of PCD layer 102 and proceeds inward. Thus, traditional elements containing a leached PCD layer 102 are often characterized as being leached to a certain depth from a given surface (hereinafter "leaching depth"). PCD, including regions of PCD layer 102, from which a substantial amount of the infiltrant has been leached is referred to as TSP.

On occasion the entire PCD 102 layer maybe leached so that it is substantially all converted to TSP, or such that a portion near every surface is converted to TSP. Substrate 104 used in the formation of PCD 102 is typically removed prior to or destroyed by this process. Such a TSP table is one type of PCD element that may be examined using methods of the present disclosure. In addition, cutters or other PCD elements in which TSP or PCD has been attached to a new substrate, similar to substrate 104, using a infiltrant may also be examined. Such cutters or PCD elements may also have been leached a second time to remove any infiltrant material that entered the PCD or TSP subsequent to any initial leaching or during the second attachment process.

Leaching is controlled to avoid contact of the acid with substrate 104 (or a similar second substrate) or interface 106 between substrate 104 and PCD layer 102. Acids sufficient to leach PCD layer 102 severely degrade the much less resistant substrate 104 and removal of infiltrant from interface 106 weakens the attachment of PCD layer 102 to substrate 104. Damage to substrate 104 undermines the physical integrity of cutter 100 and may cause it to crack, fall apart, or suffer other physical failures while in use, which may also cause other damage. Thus leaching depth profile curves may be used to determine the amount of leaching time that may result in an effective leaching depth without damaging substrate 104 or interface 106. Additionally, the leaching depth may affect properties of the PCD during use and thus is useful to know for this additional reason.

Although in the example embodiments described herein, cutters 100 are in a generally cylindrical shape with a flat surface, they may be formed in any shape suitable for their ultimate use, such as, in some embodiments, a conical shape, a variation of a cylindrical shape, or even with angles. Additionally, the surface of cutters 100 in some embodiments may be concave, convex, or irregular. Some shapes may affect the ability to determine the leaching depth of some surfaces using X-ray testing or might require some modification of the set-up using the same underlying principles for X-ray detection. Suitable shapes to test and suitable modifications of the set-up can be determined by one of ordinary skill in the art with the benefit of this disclosure.

Carefully controlling leaching of cutters 100 containing PCD layer 102 significantly adds to the complications, time, and expense of PCD manufacturing. Additionally, leaching is typically performed on batches of cutters 100. Testing to ensure proper leaching may involve slicing and polishing a representative cutter 100 and measuring the leached PCD layer 102 using a scanning electron microscope (SEM). However, such testing is destructive, time consuming, and further adds to the manufacturing cost of cutter 100. Alternatively, the use of X-rays may be used to perform non-destructive testing on cutter 100 to measure the leaching depth and residual infiltrant in PCD layer 102.

The leached portions of PCD layer 102 may as permeable or nearly as permeable to X-rays as the air surrounding cutter 100, making it difficult to identify the location of top 108 or side 110 of PCD layer 102. Without identification of top 108 and/or side 110, it may be difficult to determine the leaching depth of PCD layer 102, as measured from top 108 and/or side 110, or other properties of the leaching profile. Diamond is very permeable to X-rays, while the infiltrant is much less, allowing regions without infiltrant to be distinguished from regions containing it, thus once a boundary is established, a leaching profile may be readily generated.

An X-ray impermeable layer may be applied to top 108 or side 110 to facilitate identification of top 108 or side 110. FIG. 2A illustrates a cross-sectional side view of a TSP diamond cutter including an X-ray impermeable layer, in accordance with some embodiments of the present disclosure. X-ray impermeable layer 202 may be formed of any X-ray impermeable material, such as metal (e.g., copper, silver, lead), metal alloys, or ceramic, and may be applied to cutter 200 in any suitable manner, such as by applying a metal tape, a molten metal, coating, deposition, or by chemical vapor deposition. The thickness of X-ray impermeable layer 202 may be any thickness larger than the beam width of X-ray beam 210. X-ray impermeable layer 202 may be applied by hand or applied via an automated process.

PCD layers 204 and 206 may be similar to PCD layer 102, shown in FIG. 1. PCD layer 204 may be a layer of PCD with a reduced amount of infiltrant after a leaching process. PCD layer 206 may be a layer of PCD with where the infiltrant has not been leached. Substrate 208 may be similar to substrate 104 shown in FIG. 1.

X-ray impermeable layer 202 may be used to define top 216 of PCD layer 204 and may provide a reference point for measuring the leaching depth and the amount of residual infiltrant within the leached layer. An X-ray machine (not expressly shown) may emit X-ray beam 210 which may pass through cutter 200 and be received by X-ray detector 212. Cutter 200 may be moved through X-ray beam 210 in direction 214. X-ray detector 212 may count or record the intensity of X-ray beam 210 as it passes through each layer of cutter 200. The X-ray testing may be performed by using a point scan or a line scan. Cutter 200 may be rotated during the X-ray testing to provide data over a larger area of cutter 200. The process of X-raying cutter 200 and moving cutter 200 through X-ray beam 210 may be performed manually by an X-ray machine operator or may be performed through an automated process that feeds cutter 200 through the X-ray machine, thus increasing the safety of the X-ray testing by reducing the exposure of a human being to X-rays.

In the embodiment shown in FIG. 2A, the data recorded by X-ray detector 212 may be used to generate a leaching profile with reference to top 216 of cutter 200. The leaching profile may be used to determine the leaching depth and the residual infiltrant concentration or other leaching profile features in layers 204 and 206 of cutter 200. The data recorded by X-ray detector 212 may be input into a computer, such as leaching profile calculation system 700 shown in FIG. 7, and the computer may generate the leaching profile and calculate the leaching depth and residual infiltrant concentration or other leaching profile features.

Figure 2B:
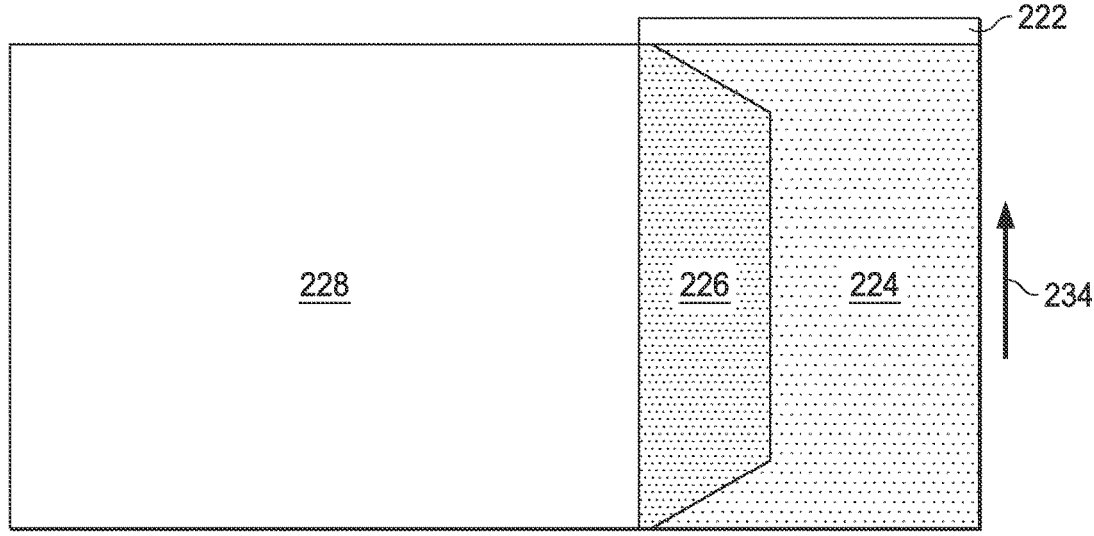
FIG. 2B illustrates a perspective view of a second embodiment of an X-ray impermeable layer applied to a TSP diamond cutter, in accordance with some embodiments of the present disclosure.

As cutter 200 is leached, leaching occurs not only from the top of cutter 200 but also from the sides of cutter 200. An X-ray impermeable layer may also be applied to the side of a cutter to measure the leaching profile from the sides of the cutter. FIG. 2B illustrates a perspective view of a second embodiment of an X-ray impermeable layer applied to a TSP diamond cutter, in accordance with some embodiments of the present disclosure. X-ray impermeable layer 222 may be applied to a side of a PCD layer in order to generate the leaching profile from the side of the PCD layer. Cutter 220 may be moved through an X-ray machine similar to the manner described with reference to FIG. 2A. The X-ray machine may emit X-ray beam 230 which pass through cutter 220 and be received by X-ray detector 232. Cutter 220 may be moved in direction 234 until the entire cutter width has passed over X-ray beam 230 and X-ray detector 232 has recorded the intensity of the X-rays.

Once X-ray testing is complete, X-ray impermeable layer 202 or 222 may remain on cutter 200 or 220 or could be easily removed by peeling, chemical treatment, etc. During a subterranean operation the forces and heat generated during the operation may wear X-ray impermeable layer 202 or 222 and expose PCD layer 204 or 224.

FIG. 3 illustrates a graph of the X-ray intensity profile of a PCD cutter leached to a depth of approximately four hundred microns, in accordance with some embodiments of the present disclosure. X-ray intensity profile 300 may be generated from the data recorded by an X-ray detector, such as X-ray detector 212 or 232, shown in FIGS. 2A and 2B, respectively. In FIG. 3, the width of the X-ray beam is approximately 100 microns and the thickness of the X-ray impermeable layer is approximately 130 microns. The intensity between point 302 and point 304 on X-ray intensity profile 300 may correspond to an X-ray beam which is not passing through any X-ray impermeable layers. This may occur before cutter enters the path between the X-ray machine and the X-ray detector. At point 304, the intensity of the X-rays received by the X-ray detector decreases until point 306. The distance between point 304 and point 306 is measured as approximately 140 microns, and corresponds to the thickness of the X-ray impermeable layer on the PCD cutter. Beginning at point 306, the intensity of the X-rays received by the X-ray detector increases for a distance and then approaches zero at point 308. The distance between point 306 and point 308 corresponds to the PCD layer and point 308 corresponds to the top of the substrate. The increased intensity of the X-rays received by the X-ray detector between approximately −0.8 and −0.6 millimeters of displacement may correspond to an area of the PCD layer that has a higher amount of infiltrant leached from the PCD layer than the area of the PCD layer corresponding to the displacement of greater than −0.6 millimeters. The distance between point 306 and point 308 is measured as approximately 550 microns. After subtracting the width of the X-ray beam, it can be determined that leached layer (e.g., layer 204 in FIG. 2A) of the cutter is approximately 450 microns.

Figure 4:
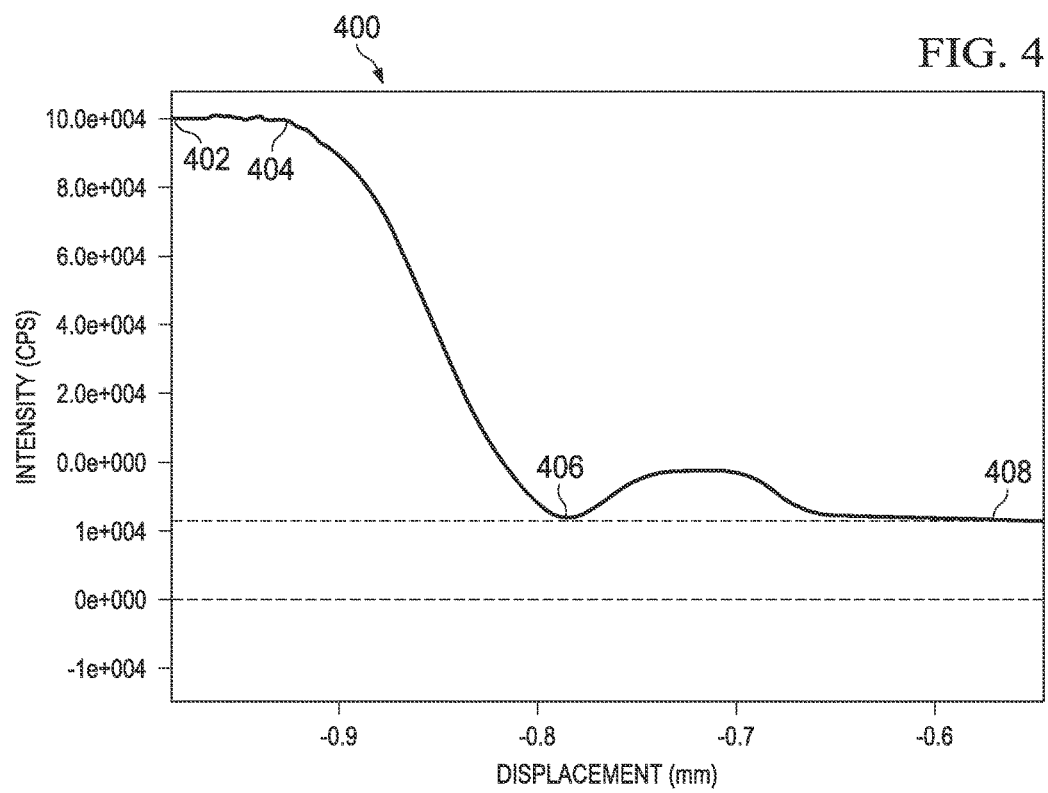
FIG. 4 illustrates a graph of the X-ray intensity profile of a PCD cutter leached to a depth of approximately one hundred microns, in accordance with some embodiments of the present disclosure.

FIG. 4 illustrates a graph of the X-ray intensity profile of a PCD cutter leached to a depth of approximately one hundred microns, in accordance with some embodiments of the present disclosure. As in FIG. 3, in FIG. 4, the width of the X-ray beam is approximately 100 microns and the thickness of the X-ray impermeable layer is approximately 130 microns. The intensity between point 402 and point 404 on X-ray intensity profile 400 may correspond to an X-ray beam which is not passing through any X-ray impermeable layers. At point 404, the intensity of the X-rays received by the X-ray detector decreases until point 406. The distance between point 404 and point 406 is measured as approximately 140 microns and corresponds to the thickness of the X-ray impermeable layer on the PCD cutter. Beginning at point 406, the intensity of the X-rays received by the X-ray detector increases for a distance and then approaches zero at point 408. The distance between point 406 and point 408 is measured as approximately 230 microns. After subtracting the width of the X-ray beam, it can be determined that leached layer of the cutter is approximately 130 microns.

Figure 5:
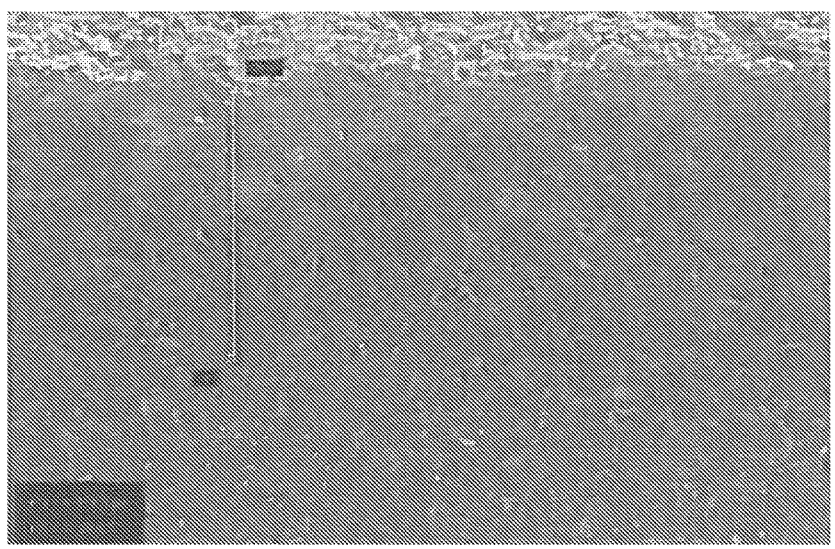
FIG. 5 illustrates a cross-sectioned image from a scanning electron microscope (SEM) of the cutter used to generate the X-ray intensity profile shown in FIG. 4, in accordance with some embodiments of the present disclosure.

FIG. 5 illustrates a cross-sectioned image from a SEM of the cutter used to generate the X-ray intensity profile shown in FIG. 4, in accordance with some embodiments of the present disclosure. The result of the leaching depth measured by the SEM is approximately 134 microns. Therefore, the X-ray measurement results in a calculated leaching depth approximately as accurate as the calculated leaching depth from the SEM measurement, but does not result in destruction of the cutter.

Figure 6:
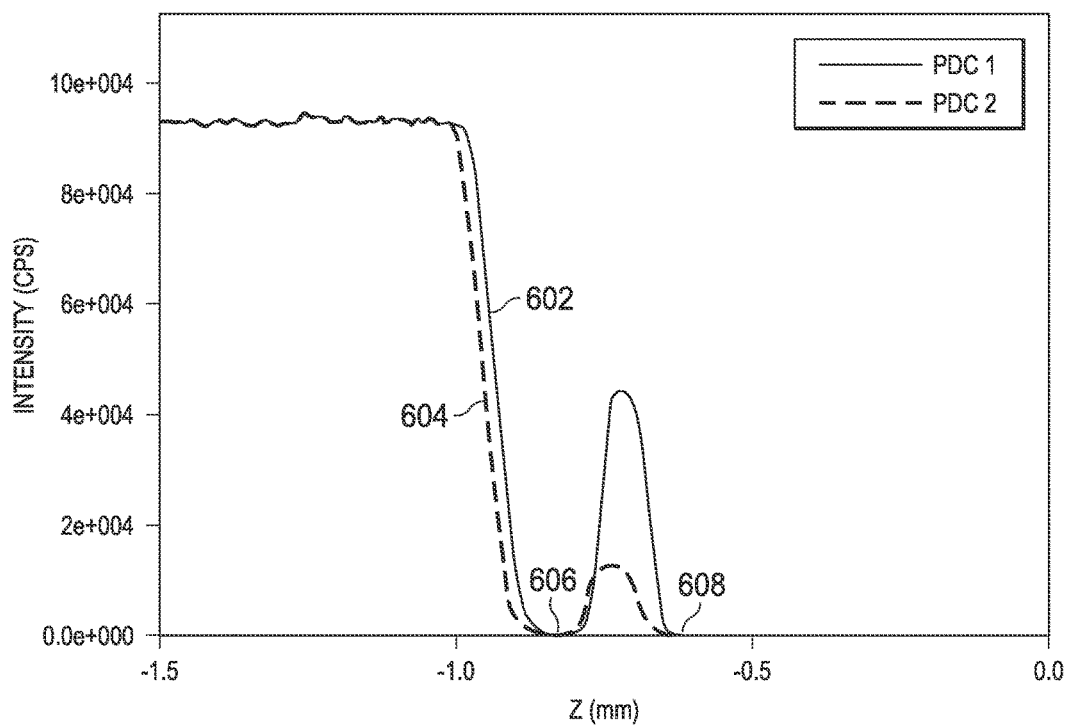
FIG. 6 illustrates X-ray intensity profiles of two PCD cutters used to determine the residual catalyst/binder/infiltrant concentration, in accordance with some embodiments of the present disclosure.

The data recorded by the X-ray detector may also be used to provide additional information about the PCD layer. FIG. 6 illustrates X-ray intensity profiles of two PCD cutters used to determine the residual infiltrant concentration, in accordance with some embodiments of the present disclosure. Line 602 corresponds to a first PCD cutter and line 604 corresponds to a second PCD cutter that may have has been sintered at a lower pressure than the first PCD cutter. There is not a significant difference between the leaching depth of the first and second cutters, as measured by the distance between points 606 and 608, where both lines 602 and 604 illustrate X-rays permeating through the cutters. However, the X-ray intensity of the first cutter, PCD1, is much higher between points 606 and 608 than the second cutter, PGD2. The only X-ray impermeable element within the PCD layer is the residual infiltrant, thus, by using information about what infiltrant was used to manufacture the PCD cutter, the intensity of the X-rays may be used to estimate the residual infiltrant concentration within the layer. In FIG. 6, the second cutter contains a higher concentration of residual infiltrant, as indicated by the lower intensity of detected X-rays, which may have been due to lower sintering pressure than the first cutter, PCD1. Actual infiltrant concentration may be determined using SEM-EDX or other methods and correlated to an X-ray impermeability to generate infiltrant concentration reference tables for a given type of cutter or PCD.

Figure 7:
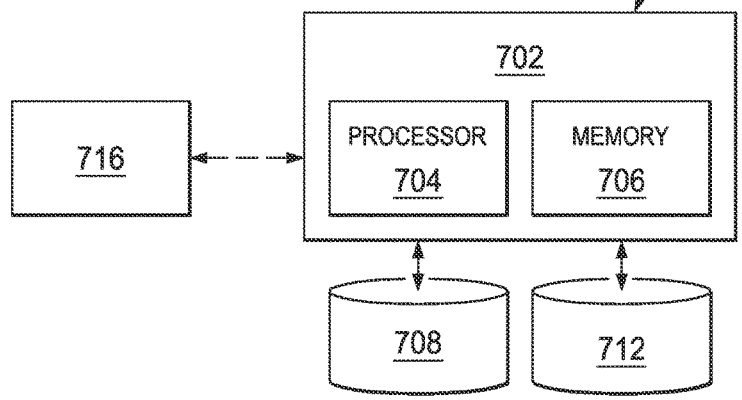
FIG. 7 illustrates a block diagram of an exemplary leaching profile calculation system, in accordance with some embodiments of the present disclosure.

FIG. 7 illustrates a block diagram of an exemplary leaching profile calculation system, in accordance with some embodiments of the present disclosure. Leaching profile calculation system 700 may be configured to calculate a leaching profile and determine the leaching depth and residual infiltrant concentration for a cutter, such as cutter 100, 200, or 220 shown in FIGS. 1, 2A, and 2B, respectively. In some embodiments, leaching profile calculation system 700 may include calculation module 702. Calculation module 702 may be used to perform the steps of method 800 as described with respect to FIG. 8. Calculation module 702 may include any suitable components. For example, in some embodiments, calculation module 702 may include processor 704. Processor 704 may include, for example a microprocessor, microcontroller, digital signal processor (DSP), application specific integrated circuit (ASIC), or any other digital or analog circuitry configured to interpret and/or execute program instructions and/or process data. In some embodiments, processor 704 may be communicatively coupled to memory 706. Processor 704 may be configured to interpret and/or execute program instructions and/or data stored in memory 706. Program instructions or data may constitute portions of software for carrying out the generation of a leaching profile and calculation of a leaching depth and residual infiltrant concentration, as described herein. Memory 706 may include any system, device, or apparatus configured to hold and/or house one or more memory modules; for example, memory 706 may include read-only memory, random access memory, solid state memory, or disk-based memory. Each memory module may include any system, device or apparatus configured to retain program instructions and/or data for a period of time (e.g., computer-readable non-transitory media).

Leaching profile calculation system 700 may further include infiltrant property database 708. Infiltrant property database 708 may be communicatively coupled to calculation module 702 and may provide values that may be used to determine the residual infiltrant concentration in response to a query or call by calculation module 702. Infiltrant property database 708 may be implemented in any suitable manner, such as by functions, instructions, logic, or code, and may be stored in, for example, a relational database, file, application programming interface, library, shared library, record, data structure, service, software-as-service, or any other suitable mechanism. Infiltrant property database 708 may include code for controlling its operation such as functions, instructions, or logic. Infiltrant property database 708 may specify any suitable parameters that may be used to calculate the residual infiltrant concentration in a cutter, such as the types of infiltrants used and/or the X-ray impermeability of various infiltrants.

Leaching profile calculation system 700 may further include X-ray profile database 708. X-ray profile database 708 may be communicatively coupled to calculation module 702 and may provide parameters for creating a leaching depth profile in response to a query or call by calculation module 702. X-ray profile database 708 may be implemented in any suitable manner, such as by functions, instructions, logic, or code, and may be stored in, for example, a relational database, file, application programming interface, library, shared library, record, data structure, service, software-as-service, or any other suitable mechanism. X-ray profile database 708 may include code for controlling its operation such as functions, instructions, or logic. X-ray profile database 708 may specify any suitable properties of an X-ray used to scan a cutter and any suitable properties of an X-ray impermeable layer applied to a surface of a cutter, such as the X-ray beam width and/or the thickness of the X-ray impermeable layer. Although leaching profile calculation system 700 is illustrated as including two databases, leaching profile calculation system 700 may contain any suitable number of databases.

In some embodiments, calculation module 702 may be configured to calculate a leaching profile and the concentration of residual infiltrant in a cutter. For example, calculation module 702 may be configured to import one or more instances of infiltrant property database 708, and/or one or more instances of X-ray profile database 708. Values from infiltrant property database 708, and/or X-ray profile database 708 may be stored in memory 706. Calculation module 702 may be further configured to cause processor 704 to execute program instructions operable to generate a leaching profile. For example, processor 704 may, based on values in infiltrant property database 708 and X-ray profile database 708, generate a leaching profile and, using the leaching profile, determine the leaching depth and calculate the residual infiltrant concentration of the cutter, as discussed in further detail with reference to FIG. 8.

Leaching profile calculation system 700 may be communicatively coupled to one or more displays 716 such that information processed by calculation module 702 (e.g., leaching profiles) may be conveyed or displayed to testers of a cutter.

Modifications, additions, or omissions may be made to FIG. 7 without departing from the scope of the present disclosure. For example, FIG. 7 shows a particular configuration of components for leaching profile calculation system 700. However, any suitable configurations of components may be used. For example, components of leaching profile calculation system 700 may be implemented either as physical or logical components. Furthermore, in some embodiments, functionality associated with components of leaching profile calculation system 700 may be implemented in special purpose circuits or components. In other embodiments, functionality associated with components of leaching profile calculation system 700 may be implemented in a general purpose circuit or components of a general purpose circuit. For example, components of leaching profile calculation system 700 may be implemented by computer program instructions.

Figure 8:
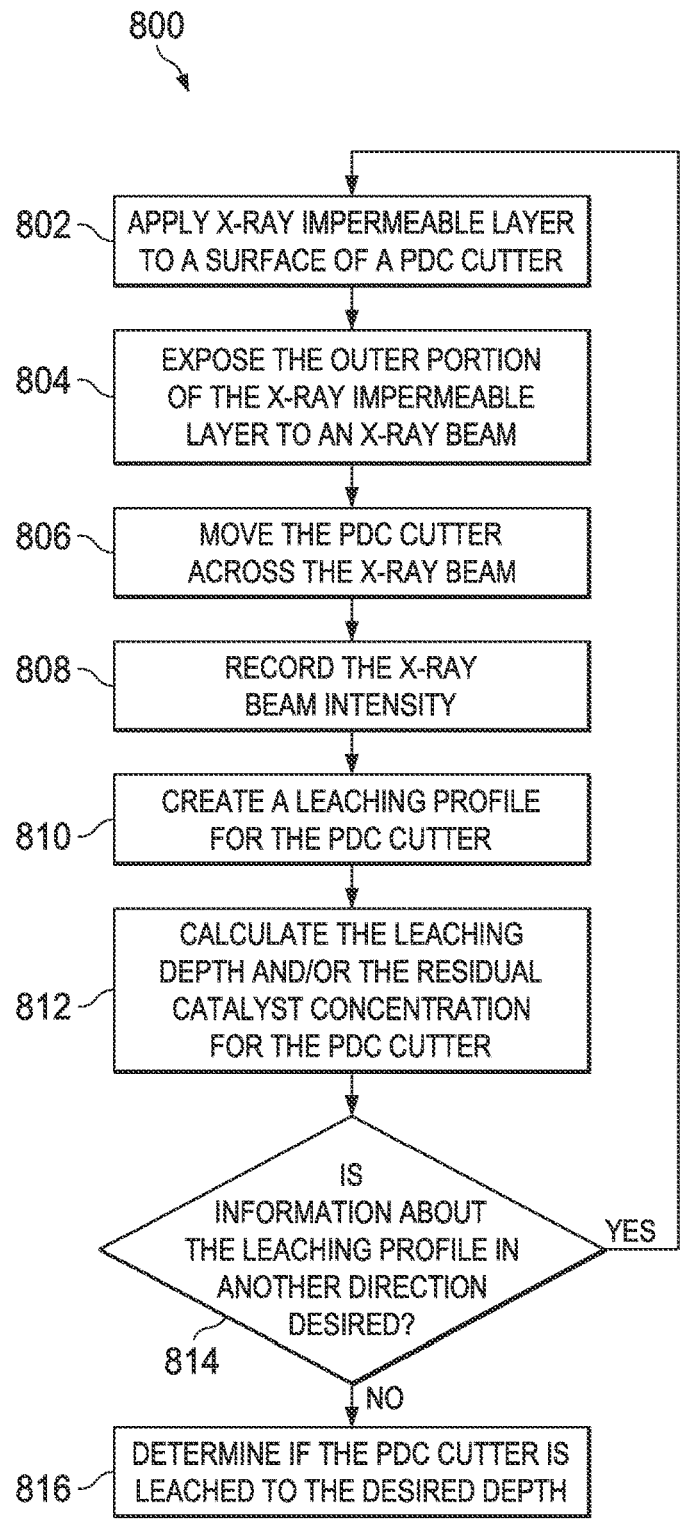
FIG. 8 illustrates a flow chart of a method for performing X-ray testing of a PCD cutter, in accordance with some embodiments of the present disclosure.

FIG. 8 illustrates a flow chart of a method for performing X-ray testing of a PCD cutter, in accordance with some embodiments of the present disclosure. The steps of method 800 may be performed by various computer programs, models, or any combination thereof, configured to perform X-ray testing of cutters, such as the calculation system illustrated in FIG. 7. For illustrative purposes, method 800 is described with respect to the cutters as illustrated in the previous FIGURES; however, method 800 may be used to create a leaching profile, determine the leaching depth, and calculate the residual infiltrant concentration for any element on a tool for use in a subterranean operation.

Method 800 may begin at step 802 where the system may apply an X-ray impermeable layer to a surface of a PCD cutter. The X-ray impermeable layer may be applied to any surface of a PCD layer of the PCD cutter, such as the top or side of the PCD layer, depending on the reference surface of the PCD cutter that will be used to generate the leaching profile. The X-ray impermeable layer may be made of any X-ray impermeable material, such as metal (e.g., copper, silver, lead) or ceramic, and may be applied to the cutter in any suitable manner, such as by applying a metal tape, a molten metal, or by chemical vapor deposition. The X-ray impermeable layer may be applied to the surface of the PCD layer in any thickness larger than the beam width of the X-ray beam that will be used to scan the PCD cutter in steps 804 and 806. The X-ray impermeable layer 200 may be applied by hand or applied via an automated process.

In step 804, the system may expose the outer portion of the X-ray impermeable layer to an X-ray beam. The X-ray impermeable layer may be used to define the beginning of the boundary of the PCD layer and provide a reference point for measuring the leaching depth profile and the amount of residual infiltrant within the leached layer in steps 810 and 812. The X-ray beam may not pass through the X-ray impermeable layer.

In step 806, the system may move the PCD cutter across the X-ray beam and in step 808, the system may detect the X-ray beam intensity while the PCD cutter is moved across the X-ray beam. As the cutter is moved through the X-ray beam, once the X-ray impermeable layer has passed through the X-ray beam, X-rays may pass through the PCD layer and be received by an X-ray detector. The X-ray detector may record the intensity of the received X-ray beam. The boundary between the X-ray impermeable layer and the PCD layer may be identified based on when X-rays begin to be detected by the X-ray detector. The X-ray beam may be a point scan or a line scan and the PCD cutter may be rotated while it is moved across the X-ray beam to provide data over a larger area of the PCD cutter. The X-ray beam may be generated, and the PCD cutter may be moved across the beam, by an automatic process. For example, a belt or other suitable conveyor system may be used to sequentially feed cutters through an X-ray system.

In step 810, the system may create a leaching profile for the PCD cutter. The leaching profile may be a plot of the intensity of the X-ray beams received by the X-ray detector versus the displacement of the PCD cutter across the X-ray beam. Examples of leaching profiles are shown in FIGS. 3, 4, and 6. A computer, such as leaching profile calculation system 700 shown in FIG. 7 may be used to create the leaching profile.

In step 812, the system may calculate the leaching depth and/or the residual infiltrant concentration for the PCD cutter based on the leaching profile. The leaching depth may be determined based on the distance between the point where the X-rays are detected by the X-ray detector after the X-ray impermeable layer has passed over the X-ray beam, and the point where the X-rays are no longer detected by the X-ray detector, such as when the substrate is over the X-ray beam. The residual infiltrant concentration may be determined based on measuring the intensity of the X-ray beams passing through the PCD layer and information about the type of metal used as a infiltrant.

In step 814, the system may determine if information about the leaching profile is desired in a different direction. For example, if the first measurement was performed with the X-ray impermeable layer applied to the top of the PCD cutter, information measured with the X-ray impermeable layer applied to the side of the PCD cutter may be desired. If information about the leaching profile is desired in a different direction, method 800 may return to step 802 to apply an X-ray impermeable layer to a different surface of the PCD cutter; otherwise, method 800 may proceed to step 816.

In step 816, the system may determine if the PCD cutter is leached to the desired depth. The desired leaching depth may be based on the requirements of the subterranean operation. The X-ray impermeable layer may remain on the cutter and may be removed during a subterranean operation by the forces and heat generated during the operation.

Modifications, additions, or omissions may be made to method 800 without departing from the scope of the present disclosure. For example, the order of the steps may be performed in a different manner than that described and some steps may be performed at the same time. Additionally, each individual step may include additional steps without departing from the scope of the present disclosure.

Methods and systems described above may be used with batch-produced cutters. In such instances, the methods and systems may be applied to all cutters in a batch or to representative cutters. Additionally, variant methods and systems may be applied to different cutters in the same batch, for instance, leaching depth of the top surface may be measured in some cutters and leaching depth from the side surface in others.

Embodiments disclosed herein include:

A. A method for detecting residual infiltrant in a leached PCD element including applying an X-ray impermeable layer to a surface of a leached PCD element with residual infiltrant, moving the element through an X-ray beam, detecting an X-ray intensity received by an X-ray detector, and generating a leaching profile of the leached PCD element based on the X-ray intensity.

B. A system for detecting residual infiltrant in a leached PCD element including a leached PCD element with residual infiltrant, an X-ray impermeable layer applied to a surface of a leached PCD element with residual infiltrant, and an X-ray testing device. The X-ray testing device may be operable to expose the leached PCD element to an X-ray beam, move the leached PCD element across the X-ray beam, detect an X-ray intensity received by an X-ray detector, and generate a leaching profile of the leached PCD element based on the X-ray intensity.

C. A non-transitory machine-readable medium comprising instructions stored therein, the instructions executable by one or more processors to facilitate performing a method for detecting residual infiltrant in an element, including applying an X-ray impermeable layer to a surface of a leached PCD element with residual infiltrant, moving the element through an X-ray beam, detecting an X-ray intensity received by an X-ray detector, and generating a leaching profile of the leached PCD element based on detected X-rays.

Each of embodiments A, B, and C may have one or more of the following additional elements in any combination: Element 1: further comprising calculating a leaching depth for the leached PCD element based on a location of the X-ray impermeable layer and the X-ray intensity. Element 2: further comprising calculating a residual infiltrant concentration for at least a portion of the leached PCD element based on an X-ray permeability of the portion of the leached PCD element. Element 3: wherein the X-ray impermeable layer is a metal tape. Element 4: wherein a thickness of the X-ray impermeable layer is greater than a width of the X-ray beam. Element 5: wherein the X-ray beam is a point scanning beam. Element 6: wherein the X-ray beam is a line scanning beam. Element 7: further comprising rotating the leached PCD element across the X-ray beam.

Although the present disclosure and its advantages have been described in detail, it should be understood that various changes, substitutions and alterations can be made herein without departing from the spirit and scope of the disclosure as defined by the following claims. For example, one of ordinary skill in the art will recognize that second or further additional substrates may be treated like substrate 104 for most purposes herein. One of ordinary skill in the art will also appreciate that any material less X-ray permeable than diamond may be detected in PCD, regardless of whether it is categorized as a infiltrant, binder, or infiltrant. For instance, impurities may be detected.

The invention claimed is:

1. A method for detecting residual infiltrant in a leached PCD element comprising:
   applying a first X-ray impermeable layer to a first surface of a leached PCD element with residual infiltrant;
   displacing the element across an X-ray beam;
   detecting an X-ray intensity received by an X-ray detector;
   generating a first leaching profile of the leached PCD element, the first leaching profile comprising a plot of X-ray intensity versus displacement of the PCD element across the X-ray beam;
   calculating a first leaching depth of the leached PCD element based on a location of the first X-ray impermeable layer and the X-ray intensity; and
   calculating a residual infiltrate concentration for at least a portion of the leached PCD element based on an X-ray permeability of the portion of the leached PCD element and a reference table for the residual infiltrant.

2. The method of claim 1, wherein the X-ray impermeable layer is a metal tape, a metal disposition, or a metal coating.

3. The method of claim 1, wherein a thickness of the X-ray impermeable layer is greater than a width of the X-ray beam.

4. The method of claim 1, wherein the X-ray beam is a point scanning beam.

5. The method of claim 1, wherein the X-ray beam is a line scanning beam.

6. The method of claim 1, further comprising rotating the leached PCD element across the X-ray beam.

7. The method of claim 1, further comprising:
   applying a second X-ray impermeable layer to a second surface of a leached PCD element with residual infiltrant;
   displacing the element across the X-ray beam;
   detecting the X-ray intensity received by the X-ray detector;
   generating a second leaching profile of the leached PCD element, the second leaching profile comprising a plot of X-ray intensity versus displacement of the PCD element across the X-ray beam; and
   calculating a second leaching depth of the leached PCD element based on a location of the second X-ray impermeable layer and the X-ray intensity.

8. The method of claim 1, wherein the reference table correlates X-ray impermeability to actual infiltrant concentration as determined by SEM-EDX.

9. A system for detecting residual infiltrant in a leached PCD element comprising:
   a leached PCD element with residual infiltrant;
   a first X-ray impermeable layer applied to a first surface of a leached PCD element with residual infiltrant; and
   an X-ray testing device operable to:
      expose the leached PCD element to an X-ray beam;
      displace the leached PCD element across the X-ray beam;
      detect an X-ray intensity received by an X-ray detector;
      generate a first leaching profile of the leached PCD element, the first leaching profile comprising a plot of X-ray intensity versus displacement of the PCD element across the X-ray beam;
      calculate a first leaching depth of the leached PCD element based on a location of the first X-ray impermeable layer and the X-ray intensity; and
      calculate a residual infiltrate concentration for at least a portion of the leached PCD element based on an X-ray permeability of the portion of the leached PCD element and a reference table for the residual infiltrant.

10. The system of claim 9, wherein the X-ray impermeable layer is a metal tape, a metal disposition, or a metal coating.

11. The system of claim 9, wherein a thickness of the X-ray impermeable layer is greater than a width of the X-ray beam.

12. The system of claim 9, wherein the X-ray beam is a point scanning beam.

13. The system of claim 9, wherein the X-ray beam is a line scanning beam.

14. The system of claim 9, the X-ray testing device is further operable to rotate the leached PCD element across the X-ray beam.

15. The system of claim 9, further comprising:
   a second X-ray impermeable layer applied to a second surface of a leached PCD element with residual infiltrant; and
   the X-ray testing device operable to:
   generate a second leaching profile of the leached PCD element the second leaching profile comprising a plot of X-ray intensity versus displacement of the PCD element across the X-ray beam; and
   calculate a second leaching depth of the leached PCD element based on a location of the first X-ray impermeable layer and the X-ray intensity.

16. The system of claim 9, wherein the reference table correlates X-ray impermeability to actual infiltrant concentration as determined by SEM-EDX.

17. A non-transitory machine-readable medium comprising instructions stored therein, the instructions executable by one or more processors to facilitate performing a method for detecting residual infiltrant in an element, the method comprising:
   applying a first X-ray impermeable layer to a first surface of a leached PCD element with residual infiltrant;
   displacing the element across an X-ray beam;
   detecting an X-ray intensity received by an X-ray detector;
   generating a first leaching profile of the leached PCD element, the first leaching profile comprising a plot of X-ray intensity versus displacement of the PCD element across the X-ray beam;
   calculating a first leaching depth of the leached PCD element based on a location of the first X-ray impermeable layer and the X-ray intensity; and calculating a residual infiltrate concentration for at least a portion of the leached PCD element based on an X-ray permeability of the portion of the leached PCD element and a reference table for the residual infiltrant.

18. The non-transitory machine-readable medium of claim 17, wherein a thickness of the X-ray impermeable layer is greater than a width of the X-ray beam.

19. The non-transitory machine-readable medium of claim 17, the method further comprising:
applying a second X-ray impermeable layer to a second surface of a leached PCD element with residual infiltrant;
displacing the element across the X-ray beam;
detecting the X-ray intensity received by the X-ray detector;
generating a second leaching profile of the leached PCD element, the second leaching profile comprising a plot of X-ray intensity versus displacement of the PCD element across the X-ray beam; and
calculating a second leaching depth of the leached PCD element based on a location of the second X-ray impermeable layer and the X-ray intensity.

20. The non-transitory machine-readable medium of claim 17, wherein the reference table correlates X-ray impermeability to actual infiltrant concentration as determined by SEM-EDX.

\* \* \* \* \*